US007713688B2

(12) United States Patent
Collins

(10) Patent No.: US 7,713,688 B2
(45) Date of Patent: May 11, 2010

(54) METHODS AND COMPOSITIONS FOR DEPLETING SPECIFIC CELL POPULATIONS FROM BLOOD TISSUES

(75) Inventor: Daniel P. Collins, Lino Lakes, MN (US)

(73) Assignee: BioE, LLC, St. Paul, MN (US)

( * ) Notice: Subject to any disclaimer, the term of this patent is extended or adjusted under 35 U.S.C. 154(b) by 329 days.

(21) Appl. No.: 11/627,762

(22) Filed: Jan. 26, 2007

(65) Prior Publication Data

US 2008/0182233 A1    Jul. 31, 2008

(51) Int. Cl.
*A01N 1/02* (2006.01)
*G01N 1/18* (2006.01)
(52) U.S. Cl. .................. 435/2; 435/7.23; 435/7.24; 435/7.25; 435/355; 435/372.1; 435/372.2; 435/372.3; 436/523; 436/529; 436/10; 436/17; 436/63; 436/64; 436/175; 436/177
(58) Field of Classification Search ................ 435/7.21, 435/7.23–7.25, 7.5, 2, 40.52, 326, 328, 355, 435/343.1, 343.2, 344, 372.1, 372.2, 372.3; 436/514, 518, 523, 529, 547, 548, 10, 16, 436/17, 18, 63, 64, 166, 175–179; 210/678, 210/806, 781, 782, 793; 530/387.7, 388.1, 530/388.8, 391.1
See application file for complete search history.

(56) References Cited

U.S. PATENT DOCUMENTS

| | | | |
|---|---|---|---|
| 5,773,224 A | 6/1998 | Grandics et al. | |
| 5,840,502 A * | 11/1998 | Van Vlasselaer | 435/7.21 |
| 6,048,715 A | 4/2000 | Haynes et al. | |
| 6,117,985 A | 9/2000 | Thomas et al. | |
| 6,280,622 B1 * | 8/2001 | Goodrich et al. | 210/252 |
| 6,448,075 B1 | 9/2002 | Thomas et al. | |
| 6,491,917 B1 | 12/2002 | Thomas et al. | |
| 6,544,751 B1 | 4/2003 | Brandwein et al. | |
| 6,933,148 B2 * | 8/2005 | Collins et al. | 435/372 |
| 7,135,335 B2 * | 11/2006 | Thomas et al. | 435/325 |
| 7,160,723 B2 * | 1/2007 | Collins et al. | 435/372 |
| 2003/0027233 A1 | 2/2003 | Collins et al. | |
| 2003/0185817 A1 | 10/2003 | Thomas et al. | |
| 2004/0062766 A1 | 4/2004 | Collins et al. | |
| 2005/0132444 A1 | 6/2005 | Xu | |
| 2007/0249047 A1 * | 10/2007 | McKenna et al. | 435/372 |

FOREIGN PATENT DOCUMENTS

| | | |
|---|---|---|
| CA | 2279474 | 1/2000 |
| EP | 0 670 185 | 9/1995 |
| EP | 0 844 482 | 5/1998 |
| JP | 2004-526452 | 9/2004 |
| WO | WO 02/083262 | 10/2002 |
| WO | WO 2004/029208 | 4/2004 |

OTHER PUBLICATIONS

Cruse et al. (Illustrated Dictionary of Immunology, CRC Press Inc 1995, pp. 157-159).*
Cruse et al., *Illustrated Dictionary of Immunology*, CRC Press Inc., 1995, pp. 157-159.
Bigbee et al., "Monoclonal antibodies specific for the M- and N-forms of human glycophorin A," *Mol. Immunol.*, 1983, 20(12):1353-1362.
Cole et al., "The EBV-Hybridoma Technique and Its Application to Human Lung Cancer," *Monoclonal Antibodies and Cancer Therapy*, 1985, Alan R. Liss, Inc, pp. 77-96.
Collins, "Cytokine and cytokine receptor expression as a biological indicator of immune activation: important considerations in the development of in vitro model systems," *J. Immunol. Meth.*, 2000, 243:125-145.
Eggens et al., "Specific Interaction between $Le^x$ and $Le^x$ Determinants. A possible basis for cell recognition in preimplantation embryos and in embryonal carcinoma cells," *J. Biol. Chem.*, 1989, 264(16):9476-9484.
Jennings et al., "CD9 cluster workshop report: cell surface binding and functional analysis," *Leukocyte Typing V*, 1995, Schlossmann et al. (eds.), Oxford University Press, Oxford, pp. 1249-1251.
Kannagi et al., "A Series of Human Erythrocyte Glycosphingolipids Reacting to the Monoclonal Antibody Directed to a Developmentally Regulated Antigen, SSEA-1," *J. Biol. Chem.*, 1982, 257(24):14865-14874.
Kohler and Milstein, "Continuous cultures of fused cells secreting antibody of predefined specificity," *Nature*, 1975, 256:495-497.
Kozbor and Roder, "The production of monoclonal antibodies from human lymphocytes," *Immunology Today*, 1983, 4:72-79.
Lanza et al., "cDNA Cloning and Expression of Platelet p24/CD9. Evidence for a new family of multiple membrane-spanning proteins," *J. Biol. Chem.*, 1991, 266(16):10638-10645.
Magnani et al., "Monoclonal Antibodies PMN 6, PMN 29, and PM-81 Bind Differently to Glycolipids Containing a Sugar Sequence Occurring in Lacto-*N*-Fucopentaose III," *Arch. Biochem., Biophys.*, 1984, 233(2):501-506.
Outram et al., "Erythromyeloid lineage fidelity is conserved in erythroleukaemia," *Leukocyte Research*, 1988, 12(8):651-657.
Rubinstein et al., "Anti-Platelet Antibody Interactions with Fcγ Receptor," *Seminars in Thrombosis and Hemostasis*, 1995, 21:10-22.
Solter and Knowles, "Monoclonal antibody defining a state-specific mouse embryonic antigen (SSEA-1)," *Proc. Natl. Acad. Sci. USA*, 1978, 75(11):5565-5569.
Telen and Bolk, "Human red cell antigens. IV. The abnormal sialoglycoprotein of Gerbich-negative red cells," *Transfusion*, 1987, 27: 309-314.
Von dem Borne and Modderman, "Reports on established clusters. Cluster report: CD9," *Leukocyte Typing IV*, 1989, Knapp et al. (eds.), Oxford University Press, Oxford, pp. 989-992.

(Continued)

*Primary Examiner*—Gailene R Gabel
(74) *Attorney, Agent, or Firm*—Fish & Richardson P.C.

(57) ABSTRACT

The invention provides compositions and methods for cell separation. These reagents and techniques specifically agglutinate cells via surface antigen recognition and can be used to recover even rare cell types in high yield.

44 Claims, No Drawings

OTHER PUBLICATIONS

Wagner, "Umbilical Cord Blood Stem Cell Transplantation," *Am. J. Ped. Hematol. Oncol.*, 1993, 15(2):169-174.

Wright and Tomlinson, "The ins and outs of the transmembrane 4 superfamily," *Immunology Today*, 1994, 15(12):588-594.

Examiner's First Report in Australian Patent Application 2002255678 dated Jul. 27, 2006, 2 pages.

First Office Action in Chinese Patent Application 02808016.5 dated Jun. 9, 2006, 14 pages.

First Examination Report in EP Application No. 02 725 093.5 dated Oct. 5, 2005, 5 pages.

Second Examination Report in EP Application No. 02 725 093.5 dated Mar. 16, 2006, 5 pages.

Third Examination Report in EP Application No. 02 725 093.5 dated Jun. 16, 2006, 5 pages.

First Examination Report in Israel Application No. 158,171 dated Apr. 20, 2007, 4 pages.

First Examination Report in Indian Application No. 01570/DELNP/2003 dated Jun. 25, 2007, 2 pages.

Official Action in Russian Application No. 2003132547 dated Feb. 9, 2006, 6 pages.

Official Action in Russian Application No. 2003132547 dated Apr. 21, 2006, 5 pages.

First Office Action in China Application No. 03825336.4 dated Dec. 1, 2006, 12 pages.

Examination Report in EU Application No. 03 759 533.7 dated Apr. 4, 2006, 4 pages.

First Examination Report in Indian Application No. 1351/DELNP/2005 dated Dec. 19, 2006, 2 pages.

Official Action in Russian Application No. 2005112731 dated Jun. 25, 2007, 4 pages.

Authorized officer Beate Giffo-Schmitt, International Preliminary Report on Patentability in PCT/US2008/051928 mailed Aug. 6, 2009, 7 pages.

* cited by examiner

METHODS AND COMPOSITIONS FOR DEPLETING SPECIFIC CELL POPULATIONS FROM BLOOD TISSUES

TECHNICAL FIELD

This invention relates to methods and compositions for separating cells, and more particularly to methods and compositions for separating cells in peripheral blood, bone marrow, umbilical cord blood and related blood tissues.

BACKGROUND

Isolation of cells for in vitro studies or for applications in cellular therapies usually incorporates an initial separation of blood cell components mainly based on the bulk depletion of erythrocytes, which comprise >99% of the cellular mass of blood. Other cell types a so are removed that provide no long-term therapeutic potential (e.g., granulocytes), contribute to pathology (e.g., T-cells in graft versus host disease (GVHD) associated with bone marrow transplant, or erythrocytes in transfusion related reactions), or, in general, interfere with the ability to monitor the cell population of interest. Depletion of T-lymphocytes from bone marrow before implantation is a common technique used to reduce the incidence or degree of GVHD, which is mediated by T-cells. Techniques used to deplete these cell populations differ depending upon the cell population that is to be removed. Complete removal of T-cells may not be desirable as they might contribute to graft vs. tumor effect. A tunable cell separation medium that can be adjusted to remove specific levels of T-cell contamination could be a useful tool for the preparation of allogeneic stem cell transplants.

Techniques for erythrocyte removal are based on hypotonic lysis of erythrocytes, density gradient separation, or enhanced centrifugal sedimentation using hydroxyethyl starch. Hypotonic lysis, while useful in low volume in vitro studies, can be impractical for the large volumes of blood tissues processed for cellular therapies. If utilized in cell therapy procedures, erythrocyte hypotonic lysis usually is done as a final clean-up step to remove the remaining erythrocytes that may contaminate a sample after bulk depletions by other methods.

Density-gradient separation relies on differences in the density of different cell types causing them to segregate at different levels in a fluid medium of variable density. Differences in density between the cell types can be small, and individual cells types can be heterogeneous in size and density. Consequently, particular cell types can become distributed throughout a density-gradient medium rather than precisely segregating at a discrete area in the density medium, resulting in reduced recovery of desired cells and/or contamination with undesired cell types. In procedures that enrich for rare blood cell types such as hematopoietic progenitor cells, density-gradient sedimentation can lead to loss or reduced yields of desired cell subsets. For example, using conventional density-gradient methods to isolate progenitor cells (e.g., CD34+ hematopoietic stem cells) from umbilical cord blood results in a significant loss of the desired stem cells. See e.g., Wagner, J. E., *Am J Ped Hematol Oncol* 15:169 (1993). As another example, using conventional density-gradient methods to isolate lymphocytes results in selective loss of particular lymphocyte subsets. See e.g., Collins, *J Immunol Methods* 243:125 (2000). These separation methods have an addition contraindication for use in cellular therapies in that the chemical entities in the separation medium can be toxic if infused with the cells into the recipient. As such, additional steps must be performed to ensure their complete removal prior to infusion. Instrument methodologies such as elutriation also depend upon differential separation of blood components by density and can suffer from similar deficiencies in performance.

An additional method for removing erythrocytes from blood includes mixing with hydroxyethyl starch (i.e., heta starch), which stimulates the formation of erythrocyte aggregates that sediment more rapidly than leukocyte components when sedimented at 50×g in a centrifuge. While this method is generally non-toxic and 'safe' for the recipient, its performance in the recovery of important cell types, including, for example, hematopoietic stem cells, is variable depending upon factors such as temperature, age of sample (post-collection) prior to processing, cellularity (concentration of cells per unit volume) of sample, volume of sample, and ratio of anti-coagulant to blood sample. These factors, with respect to umbilical cord blood, for example, can result in less-than-ideal recovery of stem cells and diminution of the engraftment potential of the cord blood cells, increasing the risk for transplant failure.

Increasing the recovery of rare cell types from donor tissue could dramatically improve the outcomes of transplant and immune therapies (e.g., bone marrow transplants, stem cell-based gene therapy, and immune cell therapy), the success of which apparently is related to the actual number of the cells being used for therapy. Additionally, with allogeneic bone marrow or cytokine-elicited stem cell transplants, implants containing the highest possible recovery of stem cells in conjunction with a partial removal of T-cells, may favor the best chance for successful transplant survival.

SUMMARY

The invention provides efficient, non-density based, non-particle based methods and compositions for separating and recovering therapeutically or diagnostically valuable cells from peripheral blood, umbilical cord blood, and bone marrow. In particular, the invention provides methods and compositions for specifically removing undesired cellular subsets that either interfere with monitoring cells of interest in vitro studies or contribute to the development of pathology when implanted. The disclosed compositions and methods can be used, for example, to efficiently prepare cells for tissue culture, immunophenotypic characterization, other diagnostic testing, further purification and therapeutic administration.

Methods of the invention include contacting a blood cell-containing sample (e.g., peripheral blood sample, umbilical cord blood sample, or bone marrow sample) with a cell separation composition. Without being bound by a particular mechanism, the invention features compositions that can selectively agglutinate cells via interaction with cell surface antigens and/or by stimulating cell-cell adherence (e.g., via increased expression of cell surface adhesion factors). Agglutinated cells partition away from un-agglutinated cells, which remain in suspension. Cells can be recovered from either the aggregate or supernatant phase. Cell recovered from the supernatant phase of the fractionated blood sample have not been biologically modified by interactions with the components of this composition. Using these compositions, even very rare cell types can be recovered in relatively high yield.

The disclosed compositions and methods can be used to isolate and enrich for a variety of cell types, including, for example, T lymphocytes, T helper cells, T suppressor cells, T killer cells, B cells, NK cells, hematopoietic stem cells, non-hematopoietic stem cells, circulating fetal cells in maternal circulation, circulating metastatic tumor cells and circulating cancer stem cells. The disclosed compositions and methods can be used in the context of allogeneic and autologous transplantation. In the context of allogeneic transplantation, T lymphocytes could be removed from the cell transplant in order to reduce T lymphocyte-associated GVHD. In the context of autologous transplantation, the disclosed compositions and methods could be used to remove undesired cells such as metastatic cancer cells from a patient's blood or bone marrow. Desirable cells (e.g., hematopoietic stem cells) then can be returned to the patient without, or substantially free of, life-threatening tumor cells. The disclosed methods can be applied to cells of any mammalian blood system including humans, non-human primates, rodents, swine, bovines and equines.

In one aspect, the invention features a composition that includes, or consists essentially, of dextran; anti-glycophorin A antibody; anti-CD9 antibody; anti-CD15 antibody; and a tandem antibody. The tandem antibody can include two different monoclonal antibodies. The tandem antibody can include any combination of IgM antibodies or IgG antibodies. The tandem antibody can include two anti-human antibodies. The concentration of the tandem antibody can be about 0.001 mg/L to about 15 mg/L. The tandem antibody can include a platelet-specific antibody other than an anti-CD9 antibody (e.g., an anti-CD41 antibody or an anti-CD61 antibody) and an antibody directed against a cell surface antigen on a different cell type. The cell surface antigen can be selected from the group consisting of CD2, CD3, CD4, CD8, CD10, CD13, CD14, CD16, CD19, CD20, CD23, CD31, CD33, CD34, CD38, CD44, CD45, CD56, CD66, CD72, CD83, CD90, CD94, CD161, and CD166. For example, the tandem antibody can include an anti-CD41 antibody and an anti-CD3 antibody; an anti-CD41 antibody and an anti-CD19 antibody; or an anti-CD41 antibody and an anti-CD8 antibody.

The composition further can include phosphate buffered saline, heparin, divalent cations (e.g., $Ca^{+2}$ or $Mg^{+2}$), or serum albumin. The pH of the composition can be between 6.8 to 7.8 (e.g., between 7.2 to 7.4). The serum albumin can be bovine serum albumin or human serum albumin. The concentration of serum albumin can be about 0.5% to about 5%.

The antibodies within the composition can be monoclonal and can be of any isotype (e.g., an IgM antibody or an IgG antibody). The antibodies within the composition can be anti-human antibodies (e.g., an anti-human glycophorin A antibody, an anti-human CD15 antibody, or an anti-human CD9 antibody). Concentration of the antibodies can be from about 0.001 mg/L to about 15 mg/L. In some embodiments, the composition includes two anti-CD9 antibodies, wherein the two anti-CD9 antibodies are different isotypes (e.g., IgG and IgM isotypes).

In another aspect, the invention features a composition that includes, or consists essentially, of dextran; heparin; divalent cations; anti-glycophorin A antibody; anti-CD9 antibody; anti-CD15 antibody; and a tandem antibody.

The invention also features a kit that includes a blood collection vessel and a cell separation composition described herein. The blood collection vessel can be a blood bag or a vacuum tube. The cell separation composition can be housed within a sterile bag. The sterile bag can be operably connected to a sterile processing bag and the sterile processing bag can be operably connected to a sterile storage bag. The sterile storage bag can include a cryopreservative.

The invention also features a composition that includes, or consists essentially of, dextran; anti-human glycophorin A antibody; anti-human CD15 antibody; and two anti-human CD9 antibodies, wherein the anti-CD9 antibodies are different isotypes (e.g., IgG and IgM isotypes).

In yet another aspect, the invention features a method for separating cells. The method includes or consists essentially of the following steps: contacting a blood cell-containing sample with a cell separation composition described herein; allowing the sample to partition into an agglutinate and a supernatant phase; and recovering cells from the agglutinate or the supernatant phase. The sample can be a human blood cell-containing sample, a peripheral blood sample, an umbilical cord sample, or a bone marrow sample. In some embodiments, cells are recovered from the supernatant phase. In other embodiments, cells are recovered from the agglutinate. In still other embodiments, cells are recovered from both the agglutinate and supernatant phase. The sample can be partitioned into the agglutinate and the supernatant phase at 1×g.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention features compositions and methods for separating cells. Compositions of the invention can be used to selectively agglutinate cells from blood cell-containing samples. Without being bound by a particular mechanism, compositions of the invention can agglutinate cells via interaction with cell surface antigens and/or by stimulating expression of cell surface adhesion factors such as LFA-1 (Lymphocyte Function-Associated Antigen-1, CD11a/CD18) and ICAM-1 (Intercellular Adhesion Molecule-1, CD54). Agglutinated cells partition away from unagglutinated cells, which remain in solution. Cells can be recovered from the supernatant or from the agglutinate.

Cell Separation Compositions

A cell separation composition in accord with the invention can contain dextran and one or more antibodies against (i.e., that have a specific binding affinity for) a cell surface antigen.

Dextran is a polysaccharide consisting of glucose units linked predominantly in alpha (1 to 6) mode. Dextran can cause stacking of erythrocytes (i.e., rouleau formation) and thereby facilitate the removal of erythroid cells from solution. Typically, the concentration of dextran in a cell separation composition is 10 to 20 g/L (e.g., 20 g/L). Antibodies against cell surface antigens can facilitate the removal of blood cells from solution via homotypic agglutination (i.e., agglutination of cells of the same cell type) and/or heterotypic agglutination (i.e., agglutination of cells of different cell types).

In some embodiments, a cell separation composition includes antibodies against glycophorin A. Typically, the concentration of anti-glycophorin A antibodies in a cell separation composition ranges from 0.1 to 15 mg/L (e.g., 0.1 to 10 mg/L, 1 to 5 mg/L, or 1 mg/L). Anti-glycophorin A antibodies can facilitate the removal of red cells from solution by at least two mechanisms. Anti-glycophorin A antibodies can cause homotypic agglutination of erythrocytes since glycophorin A is the major surface glycoprotein on erythrocytes. In addition, anti-glycophorin A antibodies also can stabilize dextran-mediated rouleau formation. Exemplary monoclonal anti-glycophorin A antibodies include, without limitation, 107FMN (Murine IgG1 Isotype), YTH89.1 (Rat IgG2b Isotype), E4 (Murine IgM Isotype), and 2.2.2.E7 (murine IgM antibody, BioE, St. Paul, Minn.). See e.g., M. Vanderlaan et al., *Molecular Immunology* 20:1353 (1983); Telen M. J. and Bolk, T. A., *Transfusion* 27:309 (1987); and Outram S. et al., *Leukocyte Research* 12:651 (1988).

In some embodiments, a cell separation composition includes antibodies against CD15. The concentration of anti-CD15 antibodies in a cell separation composition can range from 0.1 to 15 mg/L (e.g., 0.1 to 10, 1 to 5, or 1 mg/L). Anti-CD15 antibodies can cause homotypic agglutination of granulocytes by crosslinking CD15 molecules that are present on the surface of granulocytes. Anti-CD15 antibodies also can cause homotypic and heterotypic agglutination of granulocytes with monocytes, NK-cells and B-cells by stimulating expression of adhesion molecules (e.g., L-selectin and beta-2 integrin) on the surface of granulocytes that interact with adhesion molecules on monocytes, NK-cells and B-cells. Heterotypic agglutination of these cell types can facilitate the removal of these cells from solution along with red cell components. Suitable anti-CD15 antibodies can be chosen by their non-reactivity to monocytes. Exemplary monoclonal anti-CD15 antibodies include, without limitation, AHN1.1 (Murine IgM Isotype), FMC-10 (Murine IgM Isotype), BU-28 (Murine IgM Isotype), MEM-157 (Murine IgM Isotype), MEM-158 (Murine IgM Isotype), MEM-167 (Murine IgM Isotype), and 324.3.B9 (murine IgM isotype, BioE, St. Paul, Minn.). See e.g., *Leukocyte typing IV* (1989); *Leukocyte typing II* (1984); *Leukocyte typing VI* (1995); Solter D. et al., *Proc. Natl. Acad. Sci.* USA 75:5565 (1978); Kannagi, R. et al., *J. Biol. Chem.* 257:14865 (1982); Magnani, J. L. et al., Archives of Biochemistry and Biophysics 233:501 (1984); Eggens, I. et al., *J. Biol. Chem.* 264:9476 (1989).

In some embodiments, a cell separation composition includes antibodies against CD9 (e.g., at a concentration ranging from 0.1 to 15, 0.1 to 10, 1 to 5, or 1 mg/L). Anti-CD9 antibodies can cause homotypic and heterotypic agglutination of platelets. Anti-CD9 antibodies also can cause heterotypic agglutination of granulocytes and monocytes via platelets that have adhered to the surface of granulocytes and monocytes. CD9 antibodies can promote the expression of platelet p-selectin (CD62P), CD41/CD61, CD31, and CD36. Exemplary monoclonal anti-CD9 antibodies include, without limitation, MEM-61 (Murine IgG1 Isotype), MEM-62 (Murine IgG1 Isotype), MEM-192 (Murine IgM Isotype), FMC-8 (Murine IgG2a Isotype), SN4 (Murine IgG1 Isotype), BU-16 (Murine IgG2a Isotype), and 8.10.E7 (murine IgM isotope, BioE, St. Paul, Minn.). See e.g., *Leukocyte typing VI* (1995); *Leukocyte typing II* (1984); Von dem Bourne A. E. G. Kr. and Moderman P. N. (1989) In *Leukocyte typing IV* (ed. W. Knapp, et al), pp. 989-92. Oxford University Press, Oxford; Jennings, L. K., et al. In *Leukocyte typing V,* ed. S. F. Schlossmann et al., pp. 1249-51. Oxford University Press, Oxford (1995); Lanza, F. et al., *J. Biol. Chem.* 266:10638 (1991); Wright et al., *Immunology Today* 15:588 (1994); Rubinstein, E. et al., *Seminars in Thrombosis and Hemostasis* 21:10 (1995).

Compositions containing two anti-CD9 monoclonal antibodies of different isotypes are particularly useful for separating cells. For example, anti-CD9 antibodies of the IgG and IgM isotypes can be used. The IgG antibody can stimulate platelet homotypic aggregation and de-granulation via crosslinking CD9 and CD36 (FCγ1 receptor) while the IgM antibody is particularly useful for crosslinking platelets to other CD9 bearing cells such as monocytes and neutrophils. Thus, using a combination of IgG and IgM anti-CD9 antibodies can promote multiple cell linkages and thereby facilitate the aggregation and removal of platelets and any cells bound to platelets from solution. Furthermore, using the combination of the two antibodies can allow use of lower antibody concentrations than would be necessary if either antibody was used alone and can remove more platelets from the sample.

Tandem antibodies also can be included in compositions of the invention. As used herein, "tandem antibody" refers to two different antibodies that have been joined together to form a single entity capable of binding to two different antigens. A composition of the invention can include any tandem antibody or combination of tandem antibodies. Tandem antibodies can be produced using a variety of methods, including, for example, avidin-biotin bridges, bridging using anti-mouse antibodies, and chemical linkers. In particular, water soluble, heterobifunctional cross-linking reagents such as sulfo-SMCC (4-(N-Maleimidomethyl)cyclohexane-1-carboxylic acid 3-sulfo-N-hydroxysuccinimide ester, Sigma Chemical, St. Louis, Mo.), EMCS (Succinimidyl 6-maleimidylhexanoate), or EDAC (1-ethyl-3-(3-dimethylaminopropyl) carbodiimide, a bifunctional reagent that can directly link amines and carboxylate groups on different proteins) can be used. For example, to produce a tandem antibody, one antibody can be modified by the addition of sulfo-SMCC and the other antibody can be modified by the addition of 2-iminothiolane, a thiolating reagent for primary amines, or SPDP/DTT (Succinimidyl 3-(2-pyridyldithio) proprionate/Dithiothreitol). The modified antibodies can be combined in an equal molar ratio and incubated at room temperature. Tandem antibodies can be separated from single antibodies by size exclusion chromatography. Activity of the tandem antibody can be confirmed using flow cytometry to demonstrate binding of the tandem antibody to the target cells.

One of the antibodies of a tandem antibody can be a platelet-specific antibody (other than an anti-CD9 antibody) (e.g., an anti-CD41 antibody or an anti-CD61 antibody) and the other antibody can directed against a cell surface antigen expressed on a different cell type (e.g., a cell surface antigen specific for the cell to be removed). Non-limiting examples of cell surface antigens include any of the cluster designation markers (CD markers) such as CD2, CD3, CD4, C8, CD10, CD13, CD14, CD16, CD19, CD20, CD23, CD31, CD33, CD34, CD38, CD44, CD45, CD56, CD66, CD72, CD83, CD90, CD94, CD161, and CD166, or any other cell surface antigen (e.g., a cell surface protein of a tumor cell). Those with skill in the art can use routine methods to prepare antibodies against cell surface antigens of blood and other cells from humans and other mammals, including, for example a non-human primate, rodent (e.g., mice, rats, guinea pigs, hamsters, or rabbits), swine, bovine, and equine.

For example, a tandem antibody can include an anti-CD41 antibody and an anti-CD3 antibody, which facilitates the removal of T lymphocytes. Thus, in a composition containing a tandem anti-CD3/CD41 antibody in combination with dextran, anti-glycophorin A antibody, anti-CD9 antibody, and anti-CD15 antibody, the tandem anti-CD3/CD41 antibody can mediate the binding of platelets to T lymphocytes, CD9 can mediate the binding of T lymphocytes to monocytes and granulocytes via tie CD9 molecules on the surface of platelets, and CD15 can mediate the binding of monocytes and granulocytes. A blood sample processed by such a composition would be reduced for erythrocytes, granulocytes, monocytes, platelets, and T lymphocytes, and enriched for B cells and NK cells. Substituting a tandem anti-CD19/CD41 antibody for the anti-CD3/CD41 antibody can produce a cell population reduced for erythrocytes, granulocytes, monocytes, platelets and B cells and enriched for T cells and NK cells.

Concentrations of tandem antibodies can range from 0.01 to 15 mg/L (e.g., 0.1 to 15, 0.1 to 10, 1 to 5, 1, 0.8 or 0.5 mg/L). The concentration of tandem antibody can be adjusted such that a portion or substantially all of a particular cell population can be removed. See, for example, Table 4, which indicates that adding 0.8 mg/L of an anti-CD3/anti-CD41 tandem antibody to a composition containing dextran, anti-glycophorin A antibody, anti-CD9 antibody, and anti-CD15 antibody resulted in a 79.9% reduction of the CD2 population while reducing the CD16 and CD19 populations by 12.5% and 7.5% respectively. Increasing the concentration of the same tandem antibody to 2.0 mg/L in the composition resulted in an 86.7% reduction of the CD2 population while reducing the CD16 and CD19 populations by 17.5% and 17.5% respectively. Exemplary anti-CD41 antibodies include, without limitations, PLT-1 (murine IgM isotype), CN19 (murine $IgG_1$ isotype) and 8.7.C3 (murine $IgG_1$ isotype, BioE, St. Paul, Minn.). Non-limiting examples of anti-CD3 antibodies include OKT-3 (murine $IgG_1$ isotype), HIT3a (murine $IgG_{2a}$ isotype), SK7 (murine $IgG_1$ isotype), and BC3 (murine $IgG_{2a}$ isotype). Non-limiting examples of anti-CD19 antibodies include B4 (murine $IgG_1$ isotype), BU-12 (murine $IgG_1$ isotype), and HIB19 (murine $IgG_1$). Non-limiting examples of anti-CD8 antibodies include UCHT4 (murine IgG2a isotype), OKT8 (murine IgG2a isotype), RPA-T8 (murine $IgG_1$ isotype), and HIT8d (murine $IgG_1$ isotype).

Typically, antibodies used in the composition are monoclonal antibodies, which are homogenous populations of antibodies to a particular epitope contained within an antigen. Suitable monoclonal antibodies are commercially available, or can be prepared using standard hybridoma technology. In particular, monoclonal antibodies can be obtained by techniques that provide for the production of antibodies by continuous cell lines in culture, including the technique described by Kohler, G, et al., *Nature,* 1975, 256:495, the human B-cell hybridoma technique (Kosbor, et al., *Immunology Today* 4:72 (1983)), and the EBV-hybridoma technique (Cole, et al., "Monoclonal Antibodies and Cancer Therapy," Alan R. Liss, Inc, pp. 77-96 (1983)).

Antibodies can be of any immunoglobulin class including IgG, IgM, IgE, IgA, IgD, IgY, and any subclass thereof. Antibodies of the IgG and IgM isotypes are particularly useful in cell separation compositions of the invention. Pentameric IgM antibodies contain more antigen binding sites than IgG antibodies and can, in some cases (e.g., anti-glycophorin A and anti-CD15) be particularly useful for cell separation reagents by stimulating aggregation and agglutination. In other cases (e.g., anti-CD9 antibodies), antibodies of the IgG isotype are particularly useful for stimulating homotypic and/or heterotypic aggregation. Antibodies in these cell separation compositions are provided in liquid phase as soluble antibodies.

Cell separation compositions also can contain divalent cations (e.g., $Ca^{+2}$ and $Mg^{+2}$). Divalent cations can be provided, for example, by a balanced salt solution (e.g., Hank's balanced salt solution). Divalent cations are important co-factors for selectin-mediated and integrin-mediated cell-to-cell adherence.

Cell separation compositions of the invention also can contain an anticoagulant such as heparin. Heparin can prevent clotting and non-specific cell loss associated with clotting in a high calcium environment. Heparin also promotes platelet clumping. Clumped platelets can adhere to granulocytes and monocytes and thereby enhance heterotypic agglutination more so than single platelets. Heparin can be supplied as a heparin salt (e.g., sodium heparin, lithium heparin, or potassium heparin).

Cell Separation Methods

The disclosed compositions can be used, for example, to efficiently prepare cells for tissue culture, immunophenotypic characterization, diagnostic testing, further purification, and therapeutic administration. Without being bound by a particular mechanism, compositions of the invention can selectively agglutinate cells via interaction with cell surface antigens and/or by stimulating cell-cell adherence (e.g., via increased expression of cell surface adhesion factors). Agglutinated cells partition away from unagglutinated cells, which remain in solution.

After agglutination, unagglutinated cells can be recovered from the solution phase (i.e., the supernatant). Cells also can be recovered from the agglutinate. Agglutinated cells can be dissociated by, for example, transferring the cells into buffers that contain divalent cation chelators such as EDTA or EGTA. Cells recovered from the agglutinate can be further separated by using antibodies against cell surface antigens.

The disclosed compositions can be used to separate cells from a variety of blood-cell containing samples, including peripheral blood (e.g., obtained by venipuncture), umbilical cord blood (e.g., obtained post-gravida), and bone marrow (e.g., from aspirate). Blood cell-containing samples can be contacted with a cell separation composition for selective agglutination of particular types of cells. For example, erythrocytes and differentiated myeloid blood constituents can be selectively agglutinated using cell separation compositions containing antibodies to surface antigens of these cells. The disclosed compositions and methods can be used to isolate and enrich for a variety of cell types, including, for example, T lymphocytes, T helper cells, T suppressor cells, B cells, hematopoietic stem cells, circulating fetal cells in maternal circulation, and circulating metastatic tumor cells. The disclosed compositions can be used to agglutinate cells of any mammal, including humans, non-human primates, rodents, swine, bovines, and equines.

The disclosed compositions and methods can be used in the context of allogeneic and autologous transplantation. In the context of allogeneic transplantation, T lymphocytes can be removed from the cell transplant to reduce T lymphocyte-associated GVHD. In the context of autologous transplantation, the disclosed compositions and methods can be used to remove undesired cells such as metastatic cancer cells from a patient's blood or bone marrow. Desirable cells (e.g., hematopoietic stem cells) then can be returned to the patient without, or substantially free of, life-threatening tumor cells.

Cell separation compositions containing antibodies against cell surface proteins of tumor cells can be used to purge tumor cells from a patient's blood or bone marrow. Such compositions also can be used for diagnostic procedures to, for example, obtain aid detect tumor cells in a cell aggregate, where they are concentrated and are therefore more easily detectable than in circulating blood or bone marrow. In one embodiment, a cell separation composition containing antibodies against a receptor for epithelial growth factor can be used to aggregate tumor cells derived from epithelial tumors. In another embodiment, a cell separation composition containing antibodies against estrogen receptors can be used to aggregate tumor cells derived from breast and ovarian tumors. In still another embodiment, a cell separation composition containing antibodies against surface immunoglobulins can be used to aggregate tumor cells associated with chronic lymphocytic leukemia, plasmacytoma, and multiple myeloma. Breast carcinoma cells express CD15 on their cell surface and can be purged from bone marrow using cell separation compositions that contain antibodies against CD15. Other compositions can be formulated on the basis of cell type and cell surface proteins to obtain or deplete metastatic tumor cells derived from other carcinomas (e.g., erythroleukemia, endothelial carcinoma, or gastrointestinal carcinoma) from a patient's blood or bone marrow.

Cell Separation Kits

A cell separation composition can be combined with packaging material and sold as a kit. For example, a kit can include a cell separation composition that contains dextran, anti-glycophorin A antibody, anti-CD15 antibody, anti-CD9 antibody, and a tandem antibody. Such a cell separation composition also can include divalent cations and heparin. In other embodiments, a kit can include a cell separation composition that contains dextran, anti-glycophorin A antibody, anti-CD15 antibody, and two anti-CD9 antibodies of different isotypes. Such a cell separation composition also can include divalent cations and heparin.

The components of a cell separation composition can be packaged individually or in combination with one another. In some embodiments, the packaging material includes a blood collection vessel (e.g., blood bag or vacuum tube). In other embodiments, the cell separation composition can be housed within a sterile bag. Furthermore, the sterile bag can be operably connected (e.g., via sterile tubing) to a processing bag, and the processing bag can be operably connected (e.g., via sterile tubing) to a storage bag or storage vessel to facilitate processing and sterile transfer of isolated cells. The storage bag or vessel can include a cryopreservative such as dimethylsulfoxide (DMSO, typically 1 to 10%) or fetal bovine serum, human serum, or human serum albumin in combination with one or more of DMSO, trehalose, and dextran. Cryopreservation can allow for long-term storage of these cells for therapeutic or research use. The packaging material included in a kit typically contains instructions or a label describing how the cell separation composition can be used to agglutinate particular types of cells. Components and methods for producing such kits are well known.

The invention is further described in the following examples, which do not limit the scope of the invention described in the claims.

EXAMPLES

Example 1

Separating Blood Cells

This example describes the general method by which cells were separated using the cell separation reagents described below. Equal volumes of a cell separation reagent and a citrate, heparin, or ethylenediaminetetraacetic acid (EDTA) anti-coagulated blood sample (e.g., peripheral blood, cord blood, or bone marrow) were combined in a sterile closed container (e.g., a conical tube, a centrifuge tube, or blood collection bag). In experiments where samples contained white blood cell counts greater than $20 \times 10^6$ cells/mL, samples were combined in a ratio of one part blood to two parts cell separation reagent in conical tubes. Tubes were gently mixed on a rocker platform or by gentle inversion for 30 to 45 minutes at room temperature. During this mixing phase, specific cell types are stimulated to express cell surface molecules that mediate homo- and heterophillic binding into large aggregates. After completing the mixing phase, tubes were stood upright in a rack for 30 to 50 minutes to permit agglutinated cells to partition away from unagglutinated cells, which remained in suspension in the supernatant phase. A pipette was used to recover unagglutinated cells from the supernatant without disturbing the agglutinate. Recovered cells were washed in PBS+1% BSA (bovine serum albumin) or HSA (human serum albumin) or tissue culture media for further use. The cell pellet was resuspended in PBS+2% HSA for enumeration and flow cytometric analysis.

Cells also can be recovered from the agglutinate using a hypotonic lysis solution containing EDTA and ethylene glycol-bis(2-aminoethylether)-N,N,N',N'-tetraacetic acid (EGTA). The agglutinated cell phase was treated with 20:1 volumes of VitaLyse™ (BioE, St. Paul, Minn.) and vortexed to mix. After lysis of erythrocytes was complete (typically 10 minutes), leukocytes and other cells were recovered by centrifugation at 500×g for 7 minutes and the supernatant was removed. Cells were resuspended in PBS.

Recoveries of erythrocytes, leukocytes, platelets, and subsets of leukocytes were determined by enumeration of cells and their subsets by hematologic and flow cytometric analysis. Prior to flow cytometric analysis, leukocyte, erythrocyte, and platelet recoveries were determined using a Coulter Onyx Hematology Analyzer. Cell subset analysis was determined utilizing fluorescently labeled antibodies and analyzing the cells by flow cytometry using a Coulter ELITE flow cytometer. Briefly, $10^5$ separated cells or 100 μL of unseparated blood samples were stained with CD2PE, CD3FITC, CD3Cy5PE, CD4PE, CD8PE, CD14PE, CD16PE, CD19Cy5PE, CD34PE, CD45FITC, or CD45Cy5PE, or combinations of those antibodies at saturating doses for 20 minutes at room temperature. Unbound antibody was removed by washing the cells in PBS (pH 7.4). Cells were analyzed for the percentage of cells that express a particular antigen or combination of antigens. By combining the percent expression data from flow cytometry with the cell courts determined by hematology analysis, the concentration of cellular subsets can be derived. Comparing the cells recovered from the separation procedure to the cells in the original sample determines cell recovery.

Example 2

Depletion of Erythrocytes, Monocytes, Granulocytes, and Platelets from Blood Tissues The reagent described in Table 1 was used to separate cells according to the methods described in Example 1.

TABLE 1

| | |
|---|---|
| Dextran (average molecular weight 413,000 daltons) | 20 g/L |
| Hank's buffered saline solution (10X) | 100 mL/L |
| Sodium heparin (10,000 units/mL) | 1 mL/L |
| Anti-human glycophorin A (murine IgM monoclonal antibody clone 2.2.2.E7) | 1 mg/L |
| Anti-human CD15 (murine IgM monoclonal antibody clone 324.3.B9) | 2 mg/L |
| Anti-human CD9 (murine IgM monoclonal antibody clone 8.10.E7) | 1 mg/L |
| Anti-human CD9 (murine IgG monoclonal antibody clone MEM-61) | 1 mg/L |

Results of a separation on peripheral blood collected from a healthy human adult are shown in Table 2. The intention of this separation was to remove erythrocytes, monocytes, granulocytes, and platelets. Additionally, in previous experiments, there were further depletions of sub-populations of CD16+ NK cells, CD19+ B-cells, and CD3+ T-cells that were positive for CD11b and Fcγ receptors for human IgG, which were responsible for the majority of the cells depleted in the lymphocyte population. Erythrocytes were depleted ~100% (below detection limit by standard hematology analysis instrumentation) from the cells recovered from the supernatant. Lymphocytes were enriched in the supernatant relative to the monocytes and granulocytes resulting in a population that was concentrated for T-lymphocytes.

TABLE 2

|  | Before Separation | After Separation | % depletion |
|---|---|---|---|
| Erythrocytes per mL | $3.8 \times 10^9$ cells/mL | 0 | 100 |
| Leukocytes per mL | $3.7 \times 10^6$ cells/mL | $1.054 \times 10^6$/mL | 71.5 |
| Platelets per mL | $166 \times 10^6$ cells/mL | $1.09 \times 10^6$/mL | 99.3 |
| Lymphocytes (%) (absolute number) | 39.5% ($1.46 \times 10^6$/mL) | 98.1% ($1.033 \times 10^6$/mL) | 29.2 |
| Monocytes (%) (absolute number) | 10.1% ($0.37 \times 10^6$/mL) | 0.9% ($.0091 \times 10^6$/mL) | 97.7 |
| Granulocytes (%) (absolute number) | 49.8% ($0.69 \times 10^6$/mL) | 0.6% ($.0063 \times 10^6$/mL) | 99.4 |
| CD3$^+$ Lymphocytes (%) (absolute number) | 27.5% ($1.02 \times 10^6$/mL) | 72.9% ($0.765 \times 10^6$/mL) | 24.9 |

Example 3

Depletion of Erythrocytes, Monocytes, Granulocytes, Platelets and T-lymphocytes from Blood Tissues The cell separation reagent described in Table 3 was used to separate cells according to the methods described in Example 1. The tandem antibody was composed of antibody clone 8.7.C3 (anti-CD41) and clone OKT-3 (anti-CD3). Briefly, CD3 (or CD8 in some embodiments) antibodies were modified by the addition of sulfo-SMCC (Sigma, St. Louis, Mo.) at a 10× molar ratio in PBS (pH 7.3). CD41 antibodies were modified by the addition of 2-iminothiolane at a 100× molar ratio in PBS (pH 7.3). Excess unbound sulfo-SMCC and 2-iminothiolane were removed by de-salting over a sephadex G-25 column. The modified antibodies then were combined in a 1:1 molar ratio and allowed to combine overnight at room temperature. Tandem antibody was separated from single antibodies by size exclusion chromatography over Sepharose S-300HR gels. Antibody concentrations were determined by A280 and activity was confirmed by flow cytometry demonstrating platelet binding to CD3+ and CD8+ cells.

TABLE 3

| | |
|---|---|
| Dextran (average molecular weight 413,000 daltons) | 20 g/L |
| Hank's buffered saline solution (10X) | 100 mL/L |
| Sodium heparin (10,000 units/mL) | 1 mL/L |
| Anti-human glycophorin A (murine IgM monoclonal antibody clone 2.2.2.E7) | 1 mg/L |
| Anti-human CD15 (murine IgM monoclonal antibody clone 324.3.B9) | 2 mg/L |
| Anti-human CD9 (murine IgM monoclonal antibody clone 8.10.E7) | 1 mg/L |
| Anti-human CD9 (murine IgG monoclonal antibody clone MEM-61) | 1 mg/L |
| Anti-human CD41/anti-human CD3 (tandem murine IgG monoclonal) | 2 mg/L |

Table 4 contains the results of a separation performed on adult human peripheral blood samples using the formulations of Tables 1 and 3. Erythrocytes were depleted ~100% from the cells recovered from the supernatant. Additionally, monocytes, granulocytes, platelets and T-lymphocytes were significantly removed from the cells recovered from the supernatant.

TABLE 4

|  | Table 1 formulation | CD3/CD41 separation Table 3 formulation | % depletion |
|---|---|---|---|
| Erythrocytes per mL | $0.0308 \times 10^9$ cells/mL | $0^a$ | $100^a$ |
| Leukocytes per mL | $1.9 \times 10^6$ cells/mL | $0.476 \times 10^6$/mL$^a$ | $74.9^a$ |
| Platelets per mL | $1.4 \times 10^6$ cells/mL | $1.54 \times 10^6$/mL$^a$ | $-10^a$ |
| Erythrocytes per mL | $0.0308 \times 10^9$ cells/mL | $0.013 \times 10^9$/mL$^b$ | $57.8^b$ |
| Leukocytes per mL | $1.9 \times 10^6$ cells/mL | $0.406 \times 10^6$/mL$^b$ | $78.6^b$ |
| Platelets per mL | $1.4 \times 10^6$ cells/mL | $6.72 \times 10^6$/mL$^b$ | $-243^b$ |
| Lymphocytes (%) (absolute number) | 98.3% ($1.87 \times 10^6$/mL) | ND | |
| Monocytes (%) (absolute number) | 1.1% ($0.02 \times 10^6$/mL) | ND | |
| Granulocytes (%) (absolute number) | 0.6% ($0.01 \times 10^6$/mL) | ND | |
| CD2$^+$ (%) (absolute number) | 83.9% ($1.59 \times 10^6$/mL) | 68% ($0.32 \times 10^6$/mL)$^a$ | $79.9^a$ |
| CD2$^+$/CD3$^+$ (%)(absolute number) | 72.2% ($1.37 \times 10^6$/mL) | ND | |
| CD16$^+$ (%)(absolute number) | 6.4% ($0.12 \times 10^6$/mL) | 22% ($0.105 \times 10^6$/mL)$^a$ | $12.5^a$ |
| CD19$^+$ (%)(absolute number) | 4.4% ($0.08 \times 10^6$/mL) | 15.6% ($.074 \times 10^6$/mL)$^a$ | $7.5^a$ |
| CD2$^+$ (%)(absolute number) | 83.9% ($1.59 \times 10^6$/mL) | 52% ($0.211 \times 10^6$/mL)$^b$ | $86.7^b$ |
| CD2$^+$/CD3$^+$ (%)(absolute number) | 72.2% ($1.37 \times 10^6$/mL) | ND | |

TABLE 4-continued

|  | Table 1 formulation | CD3/CD41 separation Table 3 formulation | % depletion |
|---|---|---|---|
| CD16+ (%)(absolute number) | 6.4% (0.12 × 10⁶/mL) | 24.5% (0.099 × 10⁶/mL)[b] | 17.5[b] |
| CD19+ (%)(absolute number) | 4.4% (0.08 × 10⁶/mL) | 16.3% (.066 × 10⁶/mL)[b] | 17.5[b] |

[a]40% of CD3/CD41 tandem antibody concentration described in Table 3.
[b]100% of CD3/CD41 tandem antibody concentration described in Table 3.

The CD2 population found in the supernatant of peripheral blood processed by the cell separation reagent described in Table 1 is composed of 86% CD3+ cells and 14% CD3− cells. The cull separation reagent described above in Table 3 differs from the formulation of Table 1 by the addition of a tandem antibody composed of an anti-CD3 antibody and anti-CD41 antibody conjugated together. Adding 0.8 μg/mL of the tandem antibody resulted in a 79.9% reduction of the CD2 population while reducing the CD16 and CD19 populations by 12.5% and 7.5% respectively. Adding 2.0 μg/mL of the tandem antibody resulted in an 86.7% reduction of the CD2 population while reducing the CD16 and CD19 populations by 17.5% and 17.5% respectively. Because the CD3 portion of the tandem antibody effectively blocked the binding of the fluorescent reporter antibody, it prevented direct analysis of CD3 expression; in its stead CD2 was used as a proxy for enumeration of T-cells.

Example 4

Depletion of Erythrocytes, Monocytes, Granulocytes, Platelets and CD8+ T-lymphocytes from Blood Tissues The reagent described in Table 5 was used to separate cells according to the methods described in Example 1. The tandem antibody was composed of antibody clone 8.7.C3 (anti-CD41) and clone UCHT4 (anti-CD8) and was produced as described in Example 3. Results of the cell separation are shown in Table 6.

TABLE 5

| Dextran (average molecular weight 413,000 daltons) | 20 g/L |
|---|---|
| Hank's buffered saline solution (10X) | 100 mL/L |
| Sodium heparin (10,000 units/mL) | 1 mL/L |
| Anti-human glycophorin A (murine IgM monoclonal antibody clone 2.2.2.E7) | 1 mg/L |
| Anti-human CD15 (murine IgM monoclonal antibody clone 324.3.B9) | 2 mg/L |
| Anti-human CD9 (murine IgM monoclonal antibody clone 8.10.E7) | 1 mg/L |
| Anti-human CD9 (murine IgG monoclonal antibody clone MEM-61) | 1 mg/L |
| Anti-human CD41/anti-human CD8 (tandem murine IgG monoclonal) | 2 mg/L |

The T-cell component (CD3+) of lymphocytes is composed of CD4+ cells (74.4% of the CD3+ population) and CD8+ cells (24.7% of the CD3+ population). After the cell depletion step, CD4 cells comprised 89.2% of the population. Assuming that the remainder of the CD3+ population is largely comprised of CD8+ cells (pre-depletion CD4+ and CD8+ cells added together were 99.3% of CD3+ cells), 0.078×10⁶ CD8 cells would remain undepleted. This would result in an overall 68.9% depletion of CD8+ T-cells mediated by the addition of the CD8/CD41 conjugate. The direct enumeration of CD8+ T-cells by flow cytometry could not be accomplished as the CD8-directed tandem antibody used to deplete the cell population blocked the binding of the fluorescently labeled antibody. Because of this, # of CD3+-#CD4+ was used as a surrogate for the direct CD8+ count.

TABLE 6

|  | Before Separation | After Separation | % depletion |
|---|---|---|---|
| Erythrocytes per mL | 3.8 × 10⁹ cells/mL | 0 | 100 |
| Leukocytes per mL | 3.7 × 10⁶ cells/mL | 1.05 × 10⁶/mL | 71.6 |
| Platelets per mL | 166 × 10⁶ cells/mL | 20.4 × 10⁶/mL | 87.7 |
| Lymphocytes (%) (absolute number) | 39.5% (1.46 × 10⁶/mL) | 97.6% (1.025 × 10⁶/mL) | 29.8 |
| Monocytes (%) (absolute number) | 10.1% (0.37 × 10⁶/mL) | 0.9% (.0095 × 10⁶/mL) | 97.7 |
| Granulocytes (%) (absolute number) | 49.8% (0.69 × 10⁶/mL) | 1.1% (0.0115 × 10⁶/mL) | 99.4 |
| CD3+ Lymphocytes (%) (absolute number) | 27.5% (1.02 × 10⁶/mL) | 71.0% (0.745 × 10⁶/mL) | 24.9 |
| CD4+ Lymphocytes (%)(absolute number) | 20.5% (0.759 × 10⁶/mL) | 63.4% (0.666 × 10⁶/mL) | 12.2 |
| CD8+ Lymphocytes (%)(absolute number) | 6.8% (0.252 × 10⁶/mL) | ND |  |

Example 5

Depletion of CD3+ T-Lymphocytes from Human Umbilical Cord Blood Without Reduction of CD34+ Hematopoietic Stem Cells The cell separation compositions described in Table 1 and Table 3 were compared for reduction of T-lymphocytes (CD3+) and recovery of CD34+ hematopoietic stem cells. Results of a typical experiment using human umbilical cord blood are shown in Table 7.

TABLE 7

|  | Table 1 formulation | Table 3 formulation | % depletion |
|---|---|---|---|
| Erythrocytes per mL | $0 \times 10^9$ cells/mL | $0 \times 10^9$ cells/mL | 0 |
| Leukocytes per mL | $1.26 \times 10^6$ cells/mL | $0.72 \times 10^6$/mL | 42.9 |
| Platelets per mL | $3.3 \times 10^6$ cells/mL | $1.8 \times 10^6$/mL | 45.55 |
| Lymphocytes (%) (absolute number) | 98.1% ($1.24 \times 10^6$/mL) | 97.8% ($0.704 \times 10^6$/mL) | 43.3 |
| Monocytes (%) (absolute number) | 0.06% ($0.0008 \times 10^6$/mL) | 0.38% ($0.003 \times 10^6$/mL) | −275 |
| Granulocytes (%) (absolute number) | 1.46% ($0.018 \times 10^6$/mL) | 1.6% ($0.012 \times 10^6$/mL) | −33.3 |
| CD3+ Lymphocytes (%) (absolute number) | 69.1% ($0.871 \times 10^6$/mL) | 36.9% ($0.266 \times 10^6$/mL) | 69.5 |
| CD34+ Lymphocytes (%)(absolute number) | 1.02% ($0.013 \times 10^6$/mL) | 1.77% ($0.013 \times 10^6$/mL) | 0 |

Results shown in Table 7 demonstrate a 69.5% reduction in CD3+ T-lymphocytes by the addition of the CD3/CD41 tandem antibody without any reduction in the CD34+ hematopoietic cells. The use of this reagent in the processing of cord blood or similar sources of hematopoietic stem cells could help reduce the T-cell mediated GVHD experienced with hematopoietic engraftment and reconstitution.

TABLE 8

|  | Before Separation | Table 3 formulation | % depletion |
|---|---|---|---|
| Total Erythrocytes | $14.5 \times 10^9$ | $0.044 \times 10^9$ | 99.7 |
| Total Leukocytes | $57.12 \times 10^6$ | $7.19 \times 10^6$ | 87.4 |
| Total Platelets | $1752 \times 10^6$ | $46.25 \times 10^6$ | 97.4 |
| Total Lymphocytes | $31.78 \times 10^6$ | $6.99 \times 10^6$ | 78 |
| Total monocytes | $4.6 \times 10^6$ | $0.165 \times 10^6$ | 96.4 |
| Total Granulocytes | $20.74 \times 10^6$ | $0.036 \times 10^6$ | 99.8 |
| CD3+ Lymphocytes | $23.52 \times 10^6$ | ND | ND |
| CD2+ Lymphocytes | $25.3 \times 10^6$ | $1.57 \times 10^6$ | 93.8 |

The results shown in Table 8 are the result of a cell separation of a human umbilical cord blood using the cell separation medium outlined in Table 3 which utilized a CD3/CD41 tandem antibody. Pre-separation, the CD2+ co-express CD3 93% of the time. After processing, 93.8% of the CD2+ cells were depleted.

OTHER EMBODIMENTS

While the invention has been described in conjunction with the foregoing detailed description and examples, the foregoing description and examples are intended to illustrate and not to limit the scope of the amended claims. Other aspects, advantages, and modifications are within the scope of the claims.

What is claimed is:

1. A composition comprising:
   a) dextran;
   b) anti-glycophorin A antibody;
   c) two anti-CD9 antibodies of different isotypes;
   d) anti-CD 15 antibody; and
   e) a tandem antibody.

2. The composition of claim 1, wherein said tandem antibody comprises two different monoclonal antibodies.

3. The composition of claim 1, wherein said tandem antibody comprises any combination of IgM antibodies or IgG antibodies.

4. The composition of claim 1, wherein said tandem antibody comprises two anti-human antibodies.

5. The composition of claim 1, wherein the concentration of said tandem antibody is about 0.001 mg/L to about 15 mg/L.

6. The composition of claim 1, wherein said tandem antibody comprises a platelet-specific antibody other than an anti-CD9 antibody and an antibody directed against a cell surface antigen on a different cell type.

7. The composition of claim 6, wherein said platelet-specific antibody is an anti-CD 41 antibody.

8. The composition of claim 6, wherein said cell surface antigen is selected from the group consisting of CD2, CD3, CD4, CD8, CD10, CD13, CD14, CD16, CD19, CD20, CD23, CD31, CD33, CD34, CD38, CD44, CD45, CD56, CD66, CD72, CD83, CD90, CD94, CD161, and CD166.

9. The composition of claim 6, wherein said tandem antibody comprises an anti-CD 41 antibody and an anti-CD3 antibody.

10. The composition of claim 6, wherein said tandem antibody comprises an anti-CD 41 antibody and an anti-CD 19 antibody.

11. The composition of claim 6, wherein said tandem antibody comprises an anti-CD 41 antibody and an anti-CD8 antibody.

12. The composition of claim 1, further comprising phosphate buffered saline and/or heparin.

13. The composition of claim 1, further comprising divalent cations.

14. The composition of claim 13, wherein said divalent cations are $Ca^{+2}$ or $Mg^{+2}$.

15. The composition of claim 1, wherein the pH of said composition is between 6.8 to 7.8 or is between 7.2 to 7.4.

16. The composition of claim 1, wherein said anti-glycophorin A antibody is monoclonal.

17. The composition of claim 1, wherein said anti-glycophorin A antibody is an IgM antibody or an IgG antibody.

18. The composition of claim 1, wherein said anti-glycophorin A antibody is an anti-human glycophorin A antibody.

19. The composition of claim 1, wherein said anti-CD9 antibody is monoclonal.

20. The composition of claim 1, wherein said anti-CD9 antibodies are anti-human CD9 antibodies.

21. The composition of claim 1, wherein the different isotypes are IgG and IgM isotypes.

22. The composition of claim 1, wherein said anti-CD 15 antibody is monoclonal.

23. The composition of claim 1, wherein said anti-CD 15 antibody is an IgM antibody or an IgG antibody.

24. The composition of claim 1, wherein said anti-CD 15 antibody is an anti human CD15 antibody.

25. The composition of claim 1, wherein the concentration of said anti glycophorin A antibody, said anti-CD9 antibodies, or said anti-CD 15 antibody is about 0.001 mg/L to about 15 mg/L.

26. The composition of claim 1, said composition further comprising serum albumin.

27. The composition of claim 26, wherein said serum albumin is bovine serum albumin or human serum albumin.

28. The composition of claim 26, wherein the concentration of said serum albumin is about 0.5% to about 5%.

29. A composition comprising:
a) dextran;
b) heparin;
c) divalent cations;
d) anti-glycophorin A antibody;
e) two anti-CD9 antibodies of different isotypes;
f) anti-CD 15 antibody; and
g) a tandem antibody.

30. The composition of claim 29, wherein said tandem antibody comprises an anti-CD 41 antibody and an anti-CD3 antibody.

31. The composition of claim 29, wherein said tandem antibody comprises an anti-CD 41 antibody and an anti-CD 19 antibody.

32. The composition of claim 29, wherein said tandem antibody comprises an anti-CD 41 antibody and an anti-CD8 antibody.

33. A kit comprising a blood collection vessel and the cell separation composition of claim 1.

34. The kit of claim 33, wherein said blood collection vessel is a blood bag or a vacuum tube.

35. The kit of claim 33, wherein said cell separation composition of claim 1 is housed within a sterile bag.

36. The kit of claim 35, wherein said sterile bag is operably connected to a sterile processing bag and said sterile processing bag is operably connected to a sterile storage bag.

37. The kit of claim 36, wherein said sterile storage bag comprises a cryopreservative.

38. A method for separating cells, said method comprising:
a) contacting a blood cell-containing sample with a composition, said composition comprising:
i. dextran;
ii. anti-glycophorin A antibody;
iii. anti-CD9 antibodies of two different isotypes;
iv. anti-CD15 antibody; and
v. a tandem antibody;
b) allowing said sample to partition into an agglutinate and a supernatant phase; and
c) recovering cells from said agglutinate or said supernatant phase.

39. The method of claim 38, wherein said sample is a human blood cell-containing sample.

40. The method of claim 38, wherein said sample is a peripheral blood sample, an umbilical cord sample, or a bone marrow sample.

41. The method of claim 38, wherein said cells are recovered from said supernatant phase.

42. The method of claim 38, wherein said cells are recovered from said agglutinate.

43. The method of claim 38, wherein said cells are recovered from both the agglutinate and supernatant phase.

44. The method of claim 38, wherein said sample is partitioned into said agglutinate and said supernatant phase at 1 ×g.

* * * * *